(12) United States Patent
Imran et al.

(10) Patent No.: US 6,251,073 B1
(45) Date of Patent: Jun. 26, 2001

(54) MINIATURIZED ULTRASOUND APPARATUS AND METHOD

(75) Inventors: Mir A. Imran, Los Altos Hills; Glen W. McLaughlin, Saratoga; William D. Lipps, Rocklin; James M. Brennan, San Jose, all of CA (US)

(73) Assignee: Novasonics, Inc., Menlo Park, CA (US)

( * ) Notice: Subject to any disclaimer, the term of this patent is extended or adjusted under 35 U.S.C. 154(b) by 0 days.

(21) Appl. No.: 09/378,175

(22) Filed: Aug. 20, 1999

(51) Int. Cl.[7] .................................................. A61B 8/00
(52) U.S. Cl. ................................. 600/443; 600/459
(58) Field of Search .................................. 600/443, 447, 600/459; 73/625–626; 367/7, 11; 128/922, 916

(56) References Cited

U.S. PATENT DOCUMENTS 5,295,485 * 3/1994 Shinomura et al. ............... 600/443
5,483,963 * 1/1996 Butler et al. ...................... 600/447
5,817,024 * 10/1998 Ogle et al. ......................... 600/447
5,839,442 * 11/1998 Chiang et al. ..................... 600/447

* cited by examiner

*Primary Examiner*—Francis J. Jaworski
(74) *Attorney, Agent, or Firm*—Flehr Hohbach Test Albritton & Herbert LLP

(57) ABSTRACT

Ultrasound apparatus for examining tissue in a region of interest in a body comprising a housing having a viewing aperture. An ultrasonic transducer is provided comprised of an array of ultrasonic elements disposed in the viewing aperture. Electrical pulses are supplied to the transducer for transducer excitation to introduce ultrasonic signals into the body for reflection from the tissue in the region of interest. The transducer is capable of converting ultrasonic signals reflected from the tissue within the body to the transducer to provide electrical signals. The electrical signals are gain corrected in accordance with time. In-phase and out-of-phase components of the electrical signals are provided and then digitized. The digitized electrical signals are collected to form one image for a single frame of the tissue in the region of interest in the body from transducer excitations less than thirty-three in number which is then displayed.

52 Claims, 7 Drawing Sheets

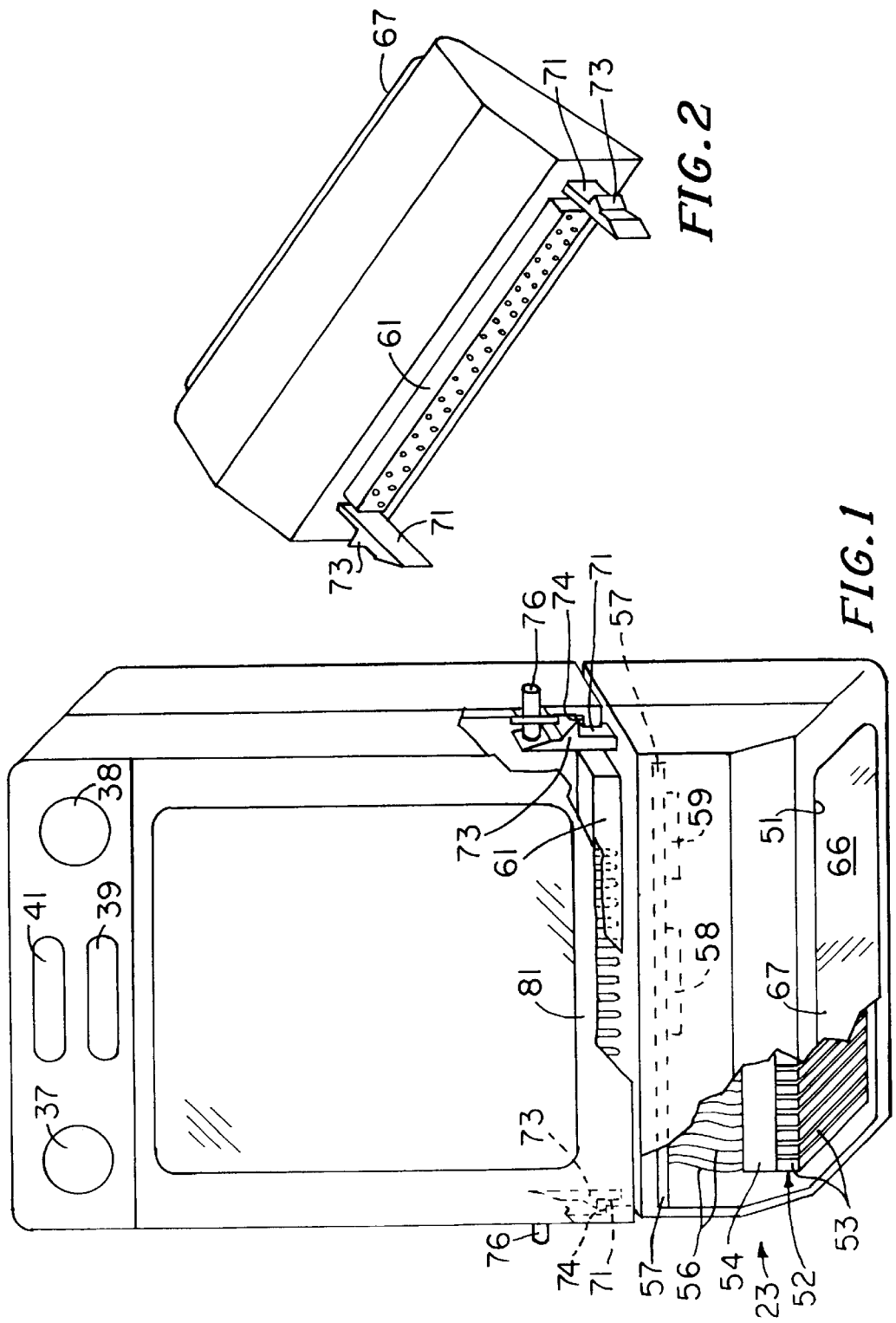

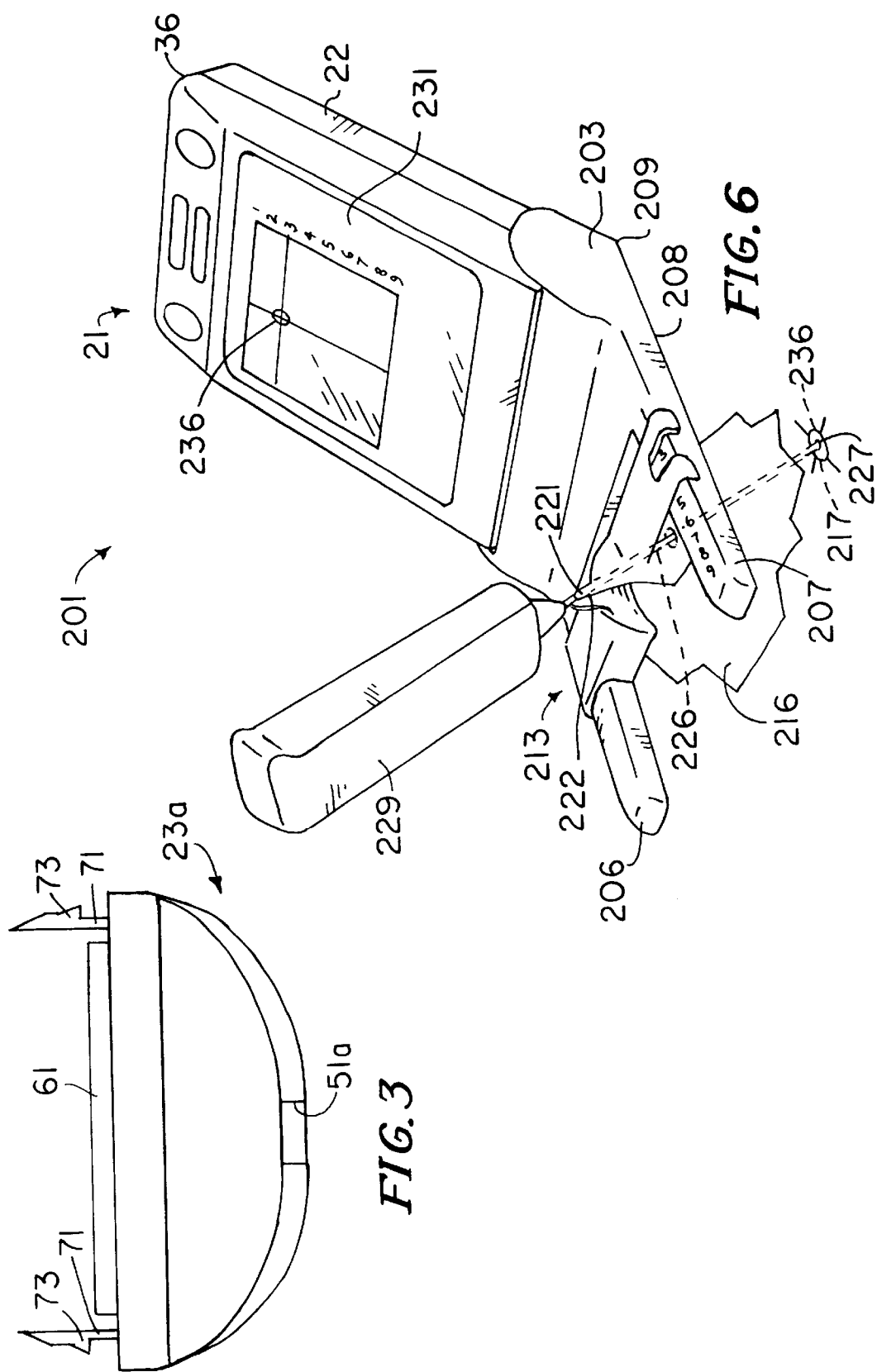

MINIATURIZED ULTRASOUND APPARATUS AND METHOD

This invention relates to a miniaturized ultrasound apparatus and method.

Ultrasound measuring apparatus of various types is in use at the present time for industrial and medical applications and particularly in medical diagnostic applications. Such apparatus, however, is often of a large size and is relatively expensive. In addition it is relatively complicated to use. There is a dramatic need for such apparatus which can be made more compact and less expensive and have greater simplicity in operation.

In general, it is an object of the present invention to provide a miniaturized ultrasound apparatus and method by which the apparatus can be greatly reduced in size and in cost.

Another object of the invention is to provide an apparatus of the above character which is portable.

Another object of the invention is to provide an apparatus of the above character which can be packaged in a pocket-sized hand-held device.

Another object of the invention is to provide an apparatus and method of the above character in which power management is used to make possible low power requirements.

Another object of the invention is to provide an apparatus and method in which detachable scan heads are utilized for selecting desired frequencies for the specific application envisioned.

Another object of the invention is to provide an apparatus and method of the above character in which a particularly novel imaging approach has been utilized to collect all the data at one time utilized for making an image in one frame from transducer excitations less than thirty-three in number to thereby reduce required the electronics and to greatly reduce power consumption.

Another object of the invention is to provide an apparatus and method of the above character in which it is possible to create a single frame per excitation of the ultrasonic transducer.

Another object of the invention is to provide an apparatus and method of the above character in which a constant pixel density is obtained.

Another object of the invention is to provide an apparatus and method of the above character in which averaging of preprocessed data can be achieved prior to image construction to provide signal-to-noise enhancement.

Another object of the invention is to provide an apparatus and method of the above character which has an extremely low duty cycle.

Another object of the invention is to provide an apparatus and method of the above character which can be utilized with linear, curved and phased arrays.

Another object of the invention is to provide an apparatus and method of the above character in which a zoom feature is provided to make possible enlargement up to the inherent resolution of the transducer array.

Another object of the invention is to provide an apparatus and method of the above character in which a non-volatile memory device is utilized in the scan head so that the associated electronics can be advised of the frequency range of the scan head.

Another object of the invention is to provide an apparatus and method of the above character which is particularly useful in directing probes such as needles to a desired site.

Another object of the invention is to provide an apparatus and method of the above character in which multiple images are provided of spaced-apart locations in the region of interest in the body.

Another object of the invention is to provide an apparatus and method of the above character in which the multiple images are spaced apart at desired intervals.

Another object of the invention is to provide an apparatus and method of the above character in which the multiple images are angularly spaced apart.

Another object of the invention is to provide an apparatus and method of the above character in which the images of the spaced-apart locations are spaced apart at proportionate intervals.

Another object of the invention is to provide an apparatus and method of the above character in which the spaced-apart images are sequentially displayed to create a kinetic image of the region of interest in the body.

Another object of the invention is to provide an apparatus and method of the above character in which the multiple images are obtained by movement of the transducer array with respect to the body.

Another object of the invention is to provide an apparatus and method of the above character which is applicable to a variety of medical diagnostic procedures.

Additional objects and features of the invention will appear from the following description in which the preferred embodiments are set forth in detail in conjunction with the accompanying drawings.

FIG. 1 is an isometric view of a miniaturized ultrasound apparatus incorporating the present invention with a detachable scan head with certain portions broken away.

FIG. 2 is an isometric view of the detachable scan head forming a part of the apparatus shown in FIG. 1 and which utilizes an ultrasonic transducer having an array.

FIG. 3 is an isometric view of an alternative detachable scan head for use with the apparatus shown in FIG. 1 which has a transducer incorporating a phased array.

FIG. 6 is an isometric view of another embodiment of the ultrasonic apparatus incorporating the present invention utilized for guiding a needle or probe.

Figure 4:
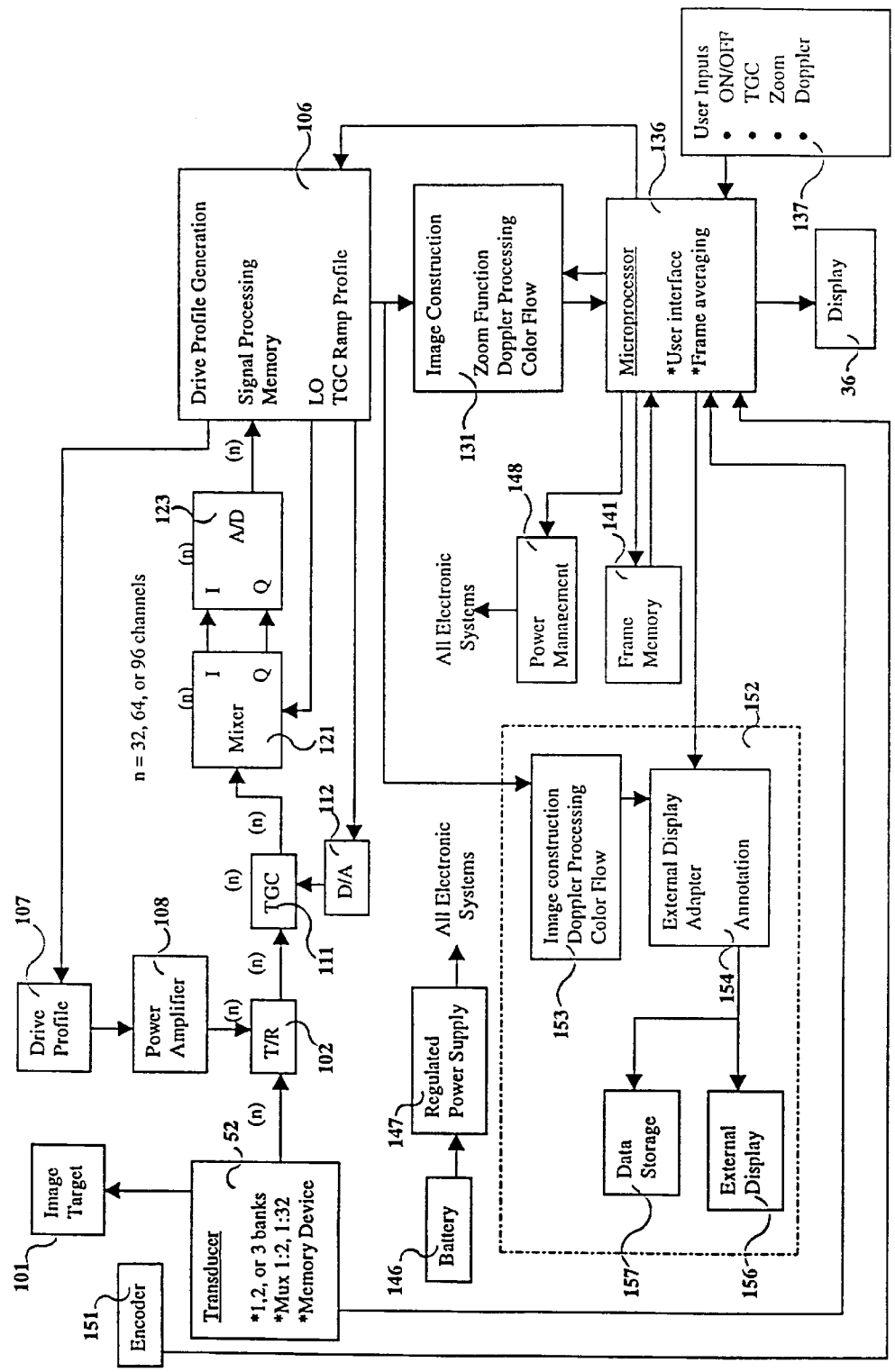
FIG. 4 is a block diagram of the electronics utilized in the apparatus shown in FIG. 1.

In general, the ultrasound apparatus of the present invention is for examining a region of interest in a body and comprises a housing having a viewing aperture. An array of transducers is disposed in the viewing aperture. Means substantially transparent to ultrasound is carried by the housing and forms an impedance matching lens overlying the transducer array and has a surface capable of being placed in contact with the body. The array of ultrasonic transducers is capable of converting ultrasonic energy reflected from within the body to the array of transducers to provide electrical signals. Means is provided for providing gain correction of the electrical signals in accordance with time. Mixing means is provided for providing in-phase and out-of-phase components of the electrical signals. Means is provided for digitizing the in- and out-of-phase components of the electrical signals. Means is provided for collecting the digitized electrical signals at one time to form one image from less than thirty-three frames of the region of interest in the body. Memory means is provided for storing the single frame in the memory means by storing the magnitude and phase angle of each received electrical signal. Display means is provided. Means is provided for coupling the single frame to the display means to provide a visual image of the region of interest in the body.

More in particular, the ultrasound apparatus 21 of the present invention as shown in FIG. 1 consists of a housing 22 which is configured in such a manner so that it can be held by a human hand. The housing 22 is provided with a detachable scan head 23. The housing 22 is externally shaped as a parallelepiped and is provided with spaced-apart parallel front and rear walls 26 and 27 and spaced apart and generally parallel side walls 28 and 29. It is also provided with a top wall 31. The bottom wall is formed by the detachable scan head 23. The housing 22 and the scan head 23 can be formed of a suitable material such as plastic.

A suitable display such as a liquid crystal display 36 is provided in the front wall. A plurality of control buttons 37, 38, 39 and 41 are provided on the front wall 26 above the display 36 and can be utilized for providing various functions as hereinafter described.

The housing 22 and the detachable scan head 23 have housed therein the electronics shown in FIG. 3. The detachable scan head 23 is one of a plurality of scan heads usable with the housing 22. As hereinafter explained, the scan heads are for use at different frequencies for different applications.

Each of the detachable scan heads 23 includes a transducer 52 which is comprised of a plurality of piezoelectric transducer elements 53 forming a transducer array. The transducer elements 53 can range in number from 32 and up with multiples thereof as for example 64, 128 and 256 elements. These elements can be formed of a conventional ultrasonic transducer material such as PZT. The transducer elements 53 can be arranged to form specific arrays as for example a linear array as shown in FIG. 1 to provide a wide footprint which is particularly useful for fetal monitoring or peripheral vascular diagnosis. Where a smaller footprint is desired, a phased array can be utilized for example when making examinations through spaced-apart ribs of a human body. Also in certain applications curved arrays can be utilized as hereinafter described.

As shown in FIGS. 1 and 2, the detachable scan head 23 is provided with a rectangular window 51 sized for a linear array and can have dimensions such as a width of 25 to 30 mm and a length of approximately 100 mm in which a transducer 52 is disposed and which is comprised of the plurality of ultrasonic transducer elements 53 to form an array of the desired configuration extending the length and width of the window 51. This array of transducer elements 53 are arranged in a conventional manner and are juxtaposed over an acoustic backing layer 54. The transducer elements 53 are connected in a conventional manner by conductors 56 to a printed circuit (PC) board 57 mounted within the scan head 23. Semiconductor switching devices 58 of a conventional type are mounted on the PC board 57 and are connected to a conventional high density, low force female connector 61 mounted in the scan head 23. A non-volatile memory device 59 of a suitable type such as an EEPROM is also mounted on the PC board 57. The non-volatile memory device 59 contains the program information with respect to the selected transducer and/or application configuration to program the electronics in the housing so that it is adapted to operate with the specific transducer array provided in the selected scan head.

A combination impedance matching layer and lens 66 formed of a suitable plastic transparent to ultrasonic energy is mounted in the window 51 and overlies the transducer 52. It is provided with a surface 67 which is adapted to engage the surface of the tissue of the body in the region of interest to be examined by the ultrasonic apparatus as hereinafter described. The matching layer and lens 66 has a y dimension which corresponds to the length of the array and an x dimension which corresponds to the width or front-to-back dimension of the array. The matching layer and lens 66 provides a fixed focus which typically has a focus near the far field or in other words near or beyond the maximum depth that the ultrasonic signal will be used to try to image the tissue while scanning in the orthogonal plane.

Cooperative means is provided for attaching the detachable scan head 23 to the housing 22 and consists of first and second upwardly and outwardly extending spring-like latch arms 71 disposed on opposite ends of the scan head 23. The arms 71 carry hooks 73 at their outermost extremities which can snap onto ledges 74 provided in the side walls 28 and 29 of the housing 22. Flanged knobs or push buttons 76 are mounted in the side walls 28 and 29 of the housing 22 for pushing the hooks 73 of the latch arms 71 off of the ledges 74 to release the scan head 23.

As the scan head 23 is pushed into the housing 22, a connection is made between the female connector 61 carried by the detachable scan head 23 and a corresponding male connector 81 provided in the housing 22. The male connector 81 is connected to the electronics within the housing 22 in a conventional manner. The scan head 23 can be detached by pressing inwardly on the arms 71 and 72 so that the hooks 73 clear the holes 76 permitting the scan head to be detached and at the same time separating the female connector 61 from the male connector 81, permitting the user to attach a different scan head 23 as desired by the user and as hereinafter explained.

Another detachable scan head is shown in FIG. 3 and is identified as a scan head 23a which is constructed in a manner similar to the scan head 23 hereinbefore described with the exception that the window 51a provided therein has a lesser length than the window 51 and typically can be approximately square and having an opening of approximately 25 mm×25 mm to receive a phased array rather than a linear array. A similar type of construction could be utilized for a curved array.

The electronics utilized in the ultrasound apparatus 21 is shown in FIG. 4 and in which the transducer array 52 is shown in contact with an image target 101 which by way of example can be tissue within a human body or tissue such as shown on the outer surface of the human body. The transducer array 52 is connected by a number of channels corresponding to the number of elements in the array to a transmit and receive switch 102, if used, typically containing a plurality of diodes that are biased on an off to perform switching between transmit and receive modes for the transducer elements 53. During the transmit mode, drive profile generation is supplied from a block 106 to a drive profile block 107 that controls a power amplifier 108 to supply energy through the transmit and receive switch 102 to the transducer elements of the transducer array 52 to cause ultrasonic energy in the form of a drive signal to be supplied into the tissue in the region of interest. Reflected ultrasonic energy in the form of a reflected signal reflected from the tissue in the region of interest is picked up by the transducer elements 53 of the transducer array. By way of example using 64 transducer elements 53 in the array of the scan head 23, drive signals can be delivered to 16 of the 64 transducer elements with time delay for focusing ultrasonic energy into a region of interest in the tissue. Reflected ultrasonic signals are picked up by all 64 of the transducer elements.

Reflected electrical signals from the transducer elements 53 are supplied to the transmit and receive switch 102 during the receive mode. The reflected signals are supplied to a time-gain correction block 111 which is used to compensate for scattering/attenuation of ultrasonic energy when penetrating deeper into the tissue. Thus the signals from the far field in the tissue are amplified in accordance with time to compensate for these losses. This time-gain correction 111 is adjustable and under user control from the time gain control (TGC) ramp profile provided in block 106 and supplied by the digital to analog (D/A) converter 112. Thus, a digitally synthesized analog ramp is created which is used for controlling the time-gain correction block 111. This TGC ramp profile provided by the digital signal processor 106 is under the control of a microprocessor 116 which is provided with a graphical user interface. Typically, the gain is increased as deeper penetration into the body is desired. The depth of penetration of course is dependent upon the detachable scan head 23 selected for the procedure.

The received reflected signals after being time-gain corrected are supplied to a quadrature mixer 121 which receives a local oscillator signal from the local oscillator in block 6. The local oscillator generates at a higher frequency than the frequency of the reflected signal. The mixer 121 delivers two heterodyne lower frequency signals at a frequency which is the difference between the reflected signal frequency and the local oscillator frequency and identified as I and Q signals with the I signal having a zero phase shift and the Q signal having a 90° (quadrature) phase shift. These two signals from the mixer 121 are supplied to analog to digital (A/D) converters 123 with one converter for the in-phase signal I and the other for the quadrature signal Q. The converted analog-to-digital signals are then supplied to a field programmable gate array 106. A suitable gate array has been found to be one supplied by Xylinx selected from the Virtex series. As shown in the block 106, this programmable gate array has a number of capabilities. For example it has a built-in memory and signal processing capabilities. It also has capabilities for generating the drive profile as well as generating the time-gain correction ramp profile. The memory provided has the capability of storing the incoming signals for a period of time which is at least sufficient to collect the raw or unprocessed data for one area with the time of collection being directly proportional to the depth of penetration of the ultrasonic energy in the image target 101. When it is found desirable, the gate array 106 can be utilized for collecting additional raw data from the A/D converters 123 as for example for collecting the raw data for the same area as for example 2 and 4 but typically less than 6 repetitive areas and then averaging the raw data to provide improved signal-to-noise data for the one area. This averaged raw data can then be stored in the same memory location. Thus the user has the capability of selecting averaging from the desired number of areas to provide preprocessed frame information.

Thus, the gate array 106 serves as a data buffer and stores the raw data until it is needed for image construction which is performed in the image construction block 131 by use of a digital signal processing (DSP) chip. One such chip found to be satisfactory is Model No. 320TMS6203 manufactured by Texas Instruments. The image construction by the DSP chip is carried out by analyzing the amplitudes of the acoustic signals being received to provide a gray scale. The operation of the digital signal processing chip 131 can be best explained by reference to the flow chart shown in FIG. 5 which describes a method by which ultrasound image reconstruction is performed in accordance with the present invention and as hereinafter described to utilize the preprocessed or raw data defining the areas to construct an image frame. Image frame construction is only one of the functions performed by the DSP chip 131. Zoom function, Doppler processing and color flow can be implemented through the DSP chip 131 under the control of the microprocessor 116. In the Doppler processing as is well known to those skilled in the art, frequency shifts between the received signal and the transmitted signal are analyzed.

The microprocessor 116 is provided with user interface and user input capabilities. It also has controls for providing image or post frame averaging and is connected to the programmable gate array 106 to make accessible to the user raw data and/or image frame averaging capabilities. The user inputs 137 as shown in FIG. 4 include ON/OFF, TGC, zoom, and Doppler functions with which the user can interface.

The raw data and/or image frame averaging which is under the control of the microprocessor 116 differs from the raw data area averaging described in connection with the gate array 106 that is performed with raw data. The raw data and/or image frame averaging by the microprocessor 116 is provided by averaging raw data and/or image frames after image frame construction and is for the purpose of smoothing the transition between image frames.

A frame memory 141 is provided which is coupled to the microprocessor 116 for storing a plurality of frames as for example 4 to 8 frames so that they can be recalled. Thus by way of example the last 5 to 8 frames can be saved in the memory for recall.

A power supply is provided for the electronics as shown in FIG. 4 and as shown therein consists of a battery 146 of a suitable type as for example a 9 volt dc battery which supplies its output to a regulator 147 to provide a regulated power supply for all of the electronics in the system as shown in FIG. 4. The power supply also includes a power management block 148 which is provided for controlling the power supplied by the battery 146 to greatly conserve battery power use. This makes possible the use of a battery having a smaller size and/or a longer life. This is made possible because all or substantially all of the semiconductor chips utilized in the electronics are provided with another terminal which can be identified as a power down or a sleep mode terminal. The microprocessor 116 acting through the power management block 148 makes decisions when certain devices i.e. parts of the electronics have performed their function and places them in sleep modes until needed to consume power. For example, when a gated burst of ultrasonic energy has been fired into the image target, the power amplifier 108 and the drive profile 107 and associated electronics can be placed in the sleep mode for low power consumption until it is time to fire another gated burst into the image target. Similarly, the time-gain correction 111, the mixer 121, and the A/D converters 123 can be placed in sleep modes once they have collected the data and supplied it to the gate array 106. Only the microprocessor 116 runs continuously since it is performing the power management. In other words, in the image construction on the display 36, all of the analog signal processing circuitry is powered down more than approximately 90% of the time the ultrasound apparatus is in operation.

The microprocessor 116 supplies the image created by digital signal processor 131 to the display 36 which as explained previously can be in the form of a liquid crystal display as shown in FIG. 1. An encoder (not shown) may be provided which can be connected to the microprocessor 116 for encoding the images on the display 36.

Auxiliary capabilities are provided in the electronics shown in FIG. 4 which are included within a dotted line rectangle 152. In block 153 provided therein, image construction, Doppler processing and color flow capabilities of the digital signal processor 131 are duplicated and supplied to an external display adapter 154 which is under the control of the microprocessor 116. The external display adapter 154 supplies data to an external display 156 which by way of example can be a large-size liquid crystal display or a conventional cathode ray tube monitor. The data is also supplied to a data storage 157 which can be utilized to provide hard copy or alternatively to store it or to supply it to a videocassette recorder or a Polaroids camera.

Figure 5:
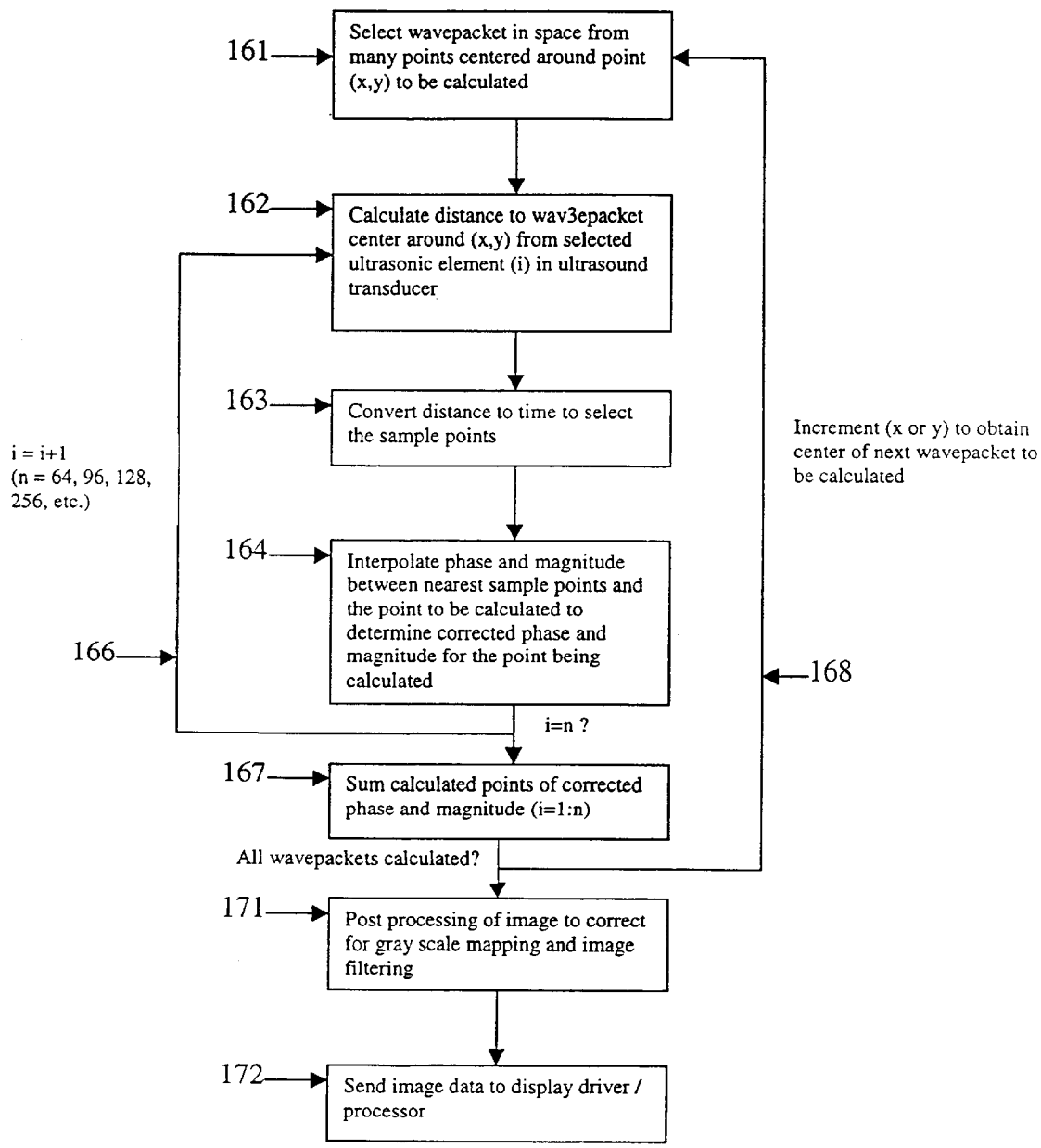
FIG. 5 is a flow chart showing the steps used for ultrasound image construction in the present apparatus and method.

Operation and use of the miniaturized ultrasound apparatus of the present invention and the method of the present invention can be described in conjunction with the flow chart shown in FIG. 5. Let it be assumed that it is desired to perform ultrasound diagnostic testing on a patient in a physician's office as for example for exploring tissue in the abdominal area serving as the image target 101. The physician takes the ultrasound apparatus 21 as shown in FIG. 1 and grasps with a hand and with a finger of that hand depresses the ON/OFF button 37 to energize the electronics. The desired detachable scan head 23 has been selected and attached to the housing 22. The non-volatile memory device 59 provided in the detachable scan head 23 programs the electronics with the housing 22 of the requirements for powering the scan head 23 within a power up time period.

The surface 67 of the detachable scan head 23 is then placed in contact with the skin of the patient overlying the abdominal area to view the tissue of interest forming the image target 101. An image appears on the liquid crystal display 36 depicting the tissue of interest being viewed. Movement of the hand-held ultrasonic apparatus 21 by the physician over the skin of the body in a desired direction will cause additional images to appear upon the liquid crystal display 36 thereby supplying to the physician various views of the image target of the patient dependent upon the position of the detachable scan head 23.

In operation of the electronics, drive profile generation from the gated array 106 supplies a single excitation in the form of a gated burst of at least one, preferably three to five cycles but typically less than six cycles, of the frequency of the selected scan head 23 to the drive profile block 107. The drive profile 107 serves as a buffer and feeds the power amplifier 108 which supplies an amplified gated burst of cycles to the transmit and receive switch 102 and thence to the transducer 52 to provide corresponding transducer excitations to produce ultrasonic pulses which are directed toward the tissue in the region of interest in the image target 101. In order to improve the performance of the apparatus in achieving high resolution images, it may be desirable to improve the signal-to-noise ratio by focusing the ultrasonic energy being introduced into the body by conventional beam forming techniques. Typically, this is accomplished by inserting appropriate time delays to selectively insonify sequential portions of the tissue in the target 101. In this way, selective regions of the tissue of interest can be insonified in a desired sequence.

Ultrasonic signals are reflected by the tissue in the region of interest and returned to the transducer 52 where they are converted into electrical signals which pass through the transmit and receive switch 102. It should be appreciated that if desired, a separate transducer can be utilized for transmission and another transducer utilized for reception rather than utilizing a single transducer as for example transducer 52 for performing both transmission and reception in connection with the transmit and receive switch 102.

The electrical signals from the transmit and receive switch 102 as hereinbefore pointed out pass through the TGC amplifier 111 through the mixer 121 to provide the in-phase and out-of-phase components I and Q of the electrical signals in an analog format. These analog signals of raw data are digitized in the A/D converter 123 and supplied to the memory in the gate array 106 where they are collected to form the image for a single area the tissue in the body from a single transducer excitation or when desired a plurality of transducer excitations less than six. This memory stores the electrical signals for the single area by storing the magnitude and phase angle and time of receipt of each received electrical signal.

In the image frame construction performed in the digital signal processor 131, the steps set forth in FIG. 5 are performed. Thus as shown in step 161 there is selected a wave packet in space of the stored electrical signals having sample points therein which are centered around a selected point or image pixel (x,y) to be calculated. Thereafter as shown in step 162 the distance to the wave packet center around (x,y) from the selected ultrasonic element in the ultrasound transducer 52 identified as (i) is calculated. Since d=rt and t=d/r where d is distance, r is rate of travel and t is time of travel, the time of travel from the tissue sample under examination can be determined by taking the known distance of travel and dividing it by the rate of travel. Distance is ascertained by using the known rate of travel of ultrasonic energy in tissue and multiplying it by time to obtain distance. Thereafter as shown in step 163 distance is converted to time to select the sample points. This is followed by step 164 by interpolating the phase and magnitude between the nearest sample points and the point to be calculated to determine the corrected phase and magnitude for that point being calculated. Thereafter, as indicated by the feedback loop 166, these same steps are performed for each of the ultrasonic elements in the array of the transducer. After all of the points have been calculated, these points are summed as shown by step 167 by considering the direction and magnitude of each vector representing a calculated point to provide a pixel value.

Thereafter, after the steps 164, 166 and 167 have been performed, x and y are incremented as shown by feedback loop 168 typically in an orderly fashion and one at a time to obtain the center of the next wave packet to be calculated until all of the x and y points have been calculated in the manner hereinbefore described. The x and y parameters are selected to provide the best image. For example, they can define a square, a rectangle or an oval shape to achieve the best image. By way of example with a 64 element transducer, five different points can be selected for each element to provide 320 points which are summed to create the desired calculated point. This procedure is continued for every point in the field of view to provide a fully constructed frame image.

After these steps have been accomplished, post processing steps can be performed as shown in FIG. 5. Thus as shown in step 171, a user gray scale correction can be performed to achieve the desired contrast. In addition image filtering can be utilized to provide edge enhancement if that is desired. Further conventional post processing steps can also be utilized which can include Doppler processing and color flow. Also as shown in FIG. 5 in step 172, image data can be supplied to a display driver or processor.

In accordance with the present invention it can be seen that digitized electrical signals are collected to form one frame from in a single area of the tissue in the region of interest from a single transducer excitation which creates a certainty in the image. As explained previously, if desired additional transducer excitations less than thirty-three can be averaged for this single area. This makes it possible to construct an image frame at a much higher rate in a much shorter time due to the fact that it is only necessary to collect a minimum amount of data i.e. that from a single transducer excitation to construct the image. Since all the information is in this single raw data areas, there is an ability to zoom in, up to the resolution of the transducer array. The apparatus and method of the present invention make it possible to provide a frame rate which is substantially higher than a conventional frame rate of 32–35 frames per second as for example from 3000 to 7000 frames per second.

With the image being constructed in the manner of the present invention with typically that digitized data only being collected for the image from a single transducer excitation, there is a reduced dosage of ultrasound energy to the patient. By the utilization of detachable scan heads, it is possible to readily select the frequency of operation and to change from a linear array to a phased array or to a curved array while retaining the same housing and electronics. Thus in the apparatus 21 there is created a modular unit which has various capabilities for diagnostic ultrasonic imaging and making it possible to create various images.

Another embodiment of an ultrasound apparatus incorporating the present invention is an ultrasound-guided probe placement apparatus 201 which is shown in FIG. 6. This apparatus includes a probe guide 202 formed of a suitable material such as plastic. The probe guide 202 consists of a body 203 which is provided with first and second parallel spaced-apart forwardly extending legs 206 and 207 that are formed integral with the body 203. The body 203 and the adjoining legs 206 and 207 are provided with a continuous lower planar surface 208 which is adapted to be placed in engagement with the skin of the patient and being movable on the skin of the patient. The body 203 is provided with an elongate transversely extending recess 211 which is formed to receive the scan head 23 of the ultrasound apparatus 21 hereinbefore described and to retain it in an angular position as for example at an angle of 45° with respect to the planar surface 208. The recess 211 opens through the bottom planar surface 208 so that the scan head 23 can come in contact with the surface of the skin 209 overlying the tissue in the region of interest in the body.

A carriage 213 is slidably mounted on the legs 206 and 207 and is movable along the length of the legs. The carriage 213 is generally in the form of a planar member 214 extending across a space 216 which is provided with a pair of spaced-apart depending flanges 217 on opposite ends of the planar member 214 and engaging the outside surfaces of the legs 206 and 207. Openings 218 are provided in planar member 214 overlying the upper surfaces of the legs 206 and 207 to make visible spaced-apart scaling indicia 219 provided on the upper surfaces of the legs 206 and 207. The indicia 219 provided on the top surfaces provide a scale reading in an incremental manner as for example from 1 to 9 on each of the legs in a direction extending away from the body 203 towards the forwardmost extremities of the legs 206 and 207. A probe guide member 221 is formed integral with the planar member 214 and extends upwardly and forwardly therefrom at a suitable angle as for example of 45°. The probe guide member 221 is provided with a longitudinally extending recess 222 which is approximately semicircular in cross section. The recess 222 is sized so as to be adapted to receive probes of various sizes such as a hypodermic needle 226 having a sharpened tip 227 and which has a syringe 229 mounted thereon. The syringe 229 can be operated by hand for withdrawing blood.

The display 36 is provided with a scale 231 corresponding to the scale formed by the indicia 219 and am also reading incrementally as for example from 1 to 9 from the top of the screen to the bottom. The display 36 is provided with a vertically extending line 233 centrally disposed between the sides of the display 36 and which is in alignment with the recess 222 provided in the probe guide 221.

Let it be assumed that it is desired to utilize the apparatus 201 as shown in FIG. 6 for withdrawing blood from a vessel below the skin of a patient as for example from a vein. The probe guide 202 of the apparatus 201 moved therein is moved over the skin 209 of the patient until the desired image appears on the screen 36. The probe guide 202 is positioned so that the image is lined up with the line 233 and is centered on the line 233. Then by observing the scale 231 and the position of the image with respect to the scale, the carriage 213 is moved to the same numerical position on the scale 219. The needle or probe 226 can then be placed in the recess 222 or alternatively the probe 226 can prior thereto be placed in the recess 222. The needle 226 can be introduced through the skin 209 at an angle determined by the probe guide member 221 and thence into the target tissue 236. This movement into the target tissue can be observed on the display 36. As soon as the target tissue 101 has been accessed, the planned-on operation as for example the withdrawal of blood, a biopsy or other procedure can be carried out utilizing a probe positioned by the use of the probe guide member 221. As soon as the procedure has been completed, the probe or needle 226 can be withdrawn, after which the probe guide 202 can be removed and placed in a different location if so desired.

Figure 8:
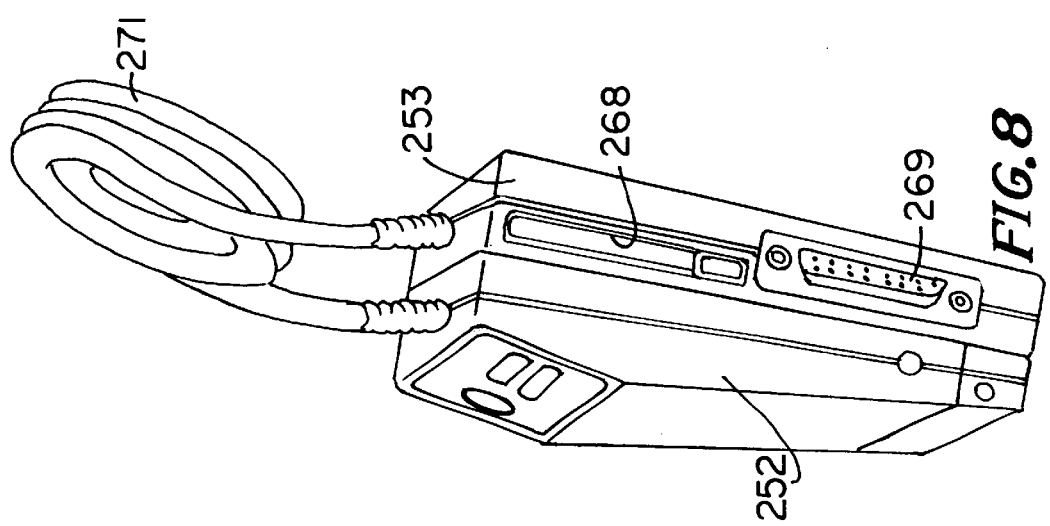
FIG. 8 is an isometric view showing the main or base module and the display module shown in FIG. 7 coupled together in a clam-shell-like manner
Figure 7:
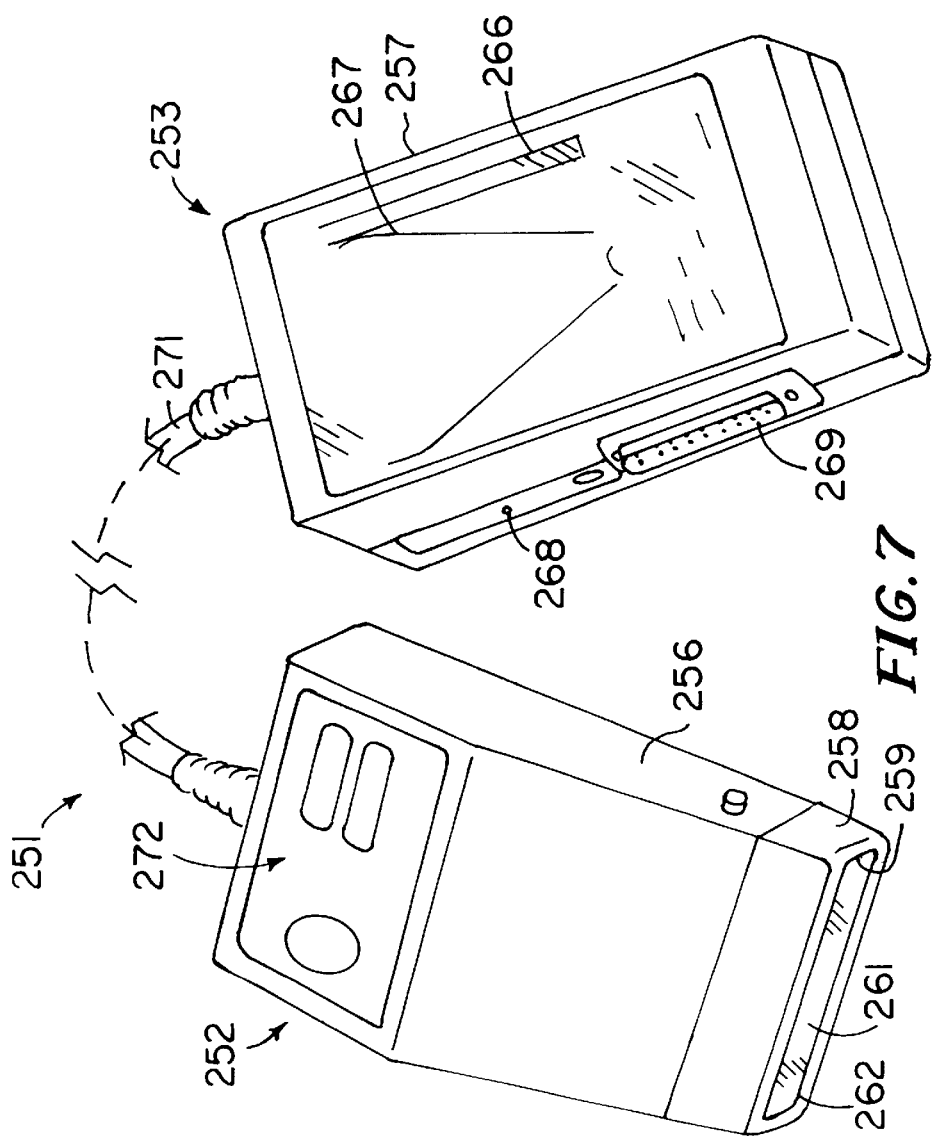
FIG. 7 is an isometric view of an ultrasonic apparatus incorporating the present invention in which a main or base module and a display module are provided.

Another embodiment of the ultrasound apparatus incorporating the present invention is shown in FIGS. 7 and 8. The ultrasonic apparatus 251 as shown therein is very similar to the ultrasound apparatus hereinbefore described in FIGS. 1, 2 and 3 with the principal difference being that the apparatus is separated into two units, one being identified as a main module 252 and the other being identified as a display module 253. These modules are provided respectively with housings 256 and 257 which are generally sized so they can fit in a human hand. The main module 252 is provided with a detachable scan head 258 similar to the detachable scan head 23 hereinbefore described. In accordance therewith it is provided with a window 259 which has a transducer 261 provided therein of the type hereinbefore described which is covered with a matching layer and lens 262 of the type hereinbefore described.

The housing 257 of the display module 253 is provided with a window 266 in which there is provided a liquid crystal display 267 similar to the LCD display 36 hereinbefore described. The housing 257 is also provided with a slot 268 for receiving a printed circuit card as for example an industry standard PCMCIA card. A connector 269 is mounted in the housing 257 and serves as a printer port for connection to a printer for printing out hard copy when that is desired. The card slot 268 also can be used for receiving a memory card for storing images for later use in a personal computer or a notebook computer.

Means is provided for establishing communication between the main module 252 and the display module 253 and consists of an umbilical cord 271. This umbilical cord 271 can be of any suitable type. To provide improved flexibility it is desirable to utilize a fiber optic cord for communication between the two modules. However, it should be appreciated that other types of an umbilical cord can be utilized as for example an electrical multi-conductor cable can be utilized. Alternatively in order to give greater flexibility and to avoid the use of a cord, a radio frequency or an infrared link can be provided between the two modules so that the display module 253 is physically free and separate from the main module 252. In this way, the main module 252 can be coupled to a wall hung display unit or alternatively connected to a conventional CRT monitor.

The main module and display module 252 and 253 can be removably fastened together as shown in FIG. 8 in a clam-shell-like fashion in a suitable manner as for example by placing Velcro® strips on the back sides of each of the housings 256 and 257 so they can be fastened together and carried as a unit while being readily separable from each other during use.

In use of the apparatus shown in FIGS. 7 and 8, the main module 252 can be taken by one hand of the physician and moved over the patient's body while the display module 253 can be held in the other hand. This makes it much easier for the physician because the display module can be held in front of his face so it is readily visible while the main module is being moved over the patient's body in locations which would make it difficult for the physician to observe the display if it were on the main module itself.

The electronics utilized in the ultrasound apparatus 251 would be very similar to the electronics used in the apparatus 21 hereinbefore described with the electronics being principally disposed within the main module 253 but interconnected by the cord 271 to any electronics provided in the display module. The controls 272 providing the user interface typically would be provided on the main module 252. However, it should be appreciated that if desired at least some of the controls if desired could be provided on the display module.

Figure 9:
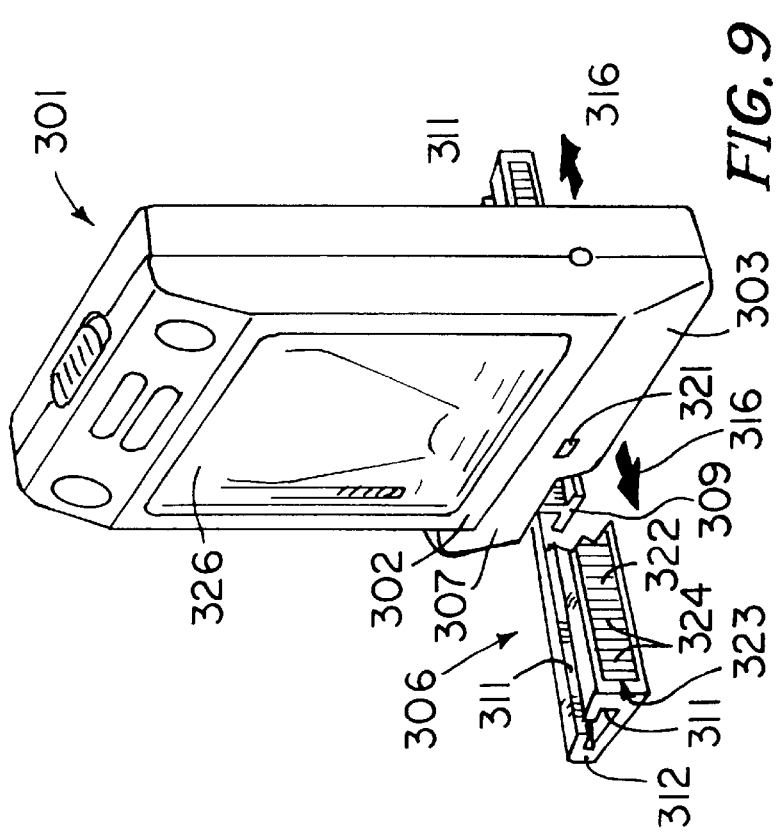
FIG. 9 is an isometric view of another embodiment of the ultrasound apparatus of the present invention which incorporates the use of linear spatial imaging.

In certain applications of the ultrasonic apparatus of the present invention it may be desirable to obtain multiple images of the target tissue to make possible a kinetic display to aid the physician in making a diagnosis. Ultrasonic apparatus 301 utilized for such a purpose is shown in FIG. 9. As shown therein, the ultrasound apparatus 301 has a housing 302 of the type hereinbefore described which is adapted to be held by the human hand and which is provided with a detachable scan head 303. The housing 302 and the scan head 303 can be generally of the same type as housing 22 and the detachable scan head 23 hereinbefore described. The scan head 303, however, is provided with a triggering mechanism 306 so that an image set will only be taken when a triggering event has occurred rather than taking images continuously as for example at 20 frames a second. The triggering mechanism 306 is utilized to create images at different spatial intervals which are recorded in memory so that they can be played back in an endless loop fashion to provide a kinetic image of the tissue being visualized. Thus, by way of example if a tumor in the body is being imaged, taking images at different spatial intervals at different times makes it possible to ascertain whether or not a tumor is growing or shrinking.

As shown in FIG. 9, this triggering mechanism 306 can consist of an attachment 307 provided at one end of the scan head 303 and as shown forming an integral part thereof. This attachment 307 includes a T-shaped foot 309 that is slidably mounted in a T-shaped slot 311 provided in an elongate support member 312 that serves as a support and guide for the scan head 303 and the housing 302 to which it is attached. The support member 312 is provided with a lower surface 313 which is adapted to be placed upon the skin overlying the tissue of the human body being examined. When so positioned, the attachment 307 with its scan head and housing 303 and 302 can be moved longitudinally of the member in the T-shaped slot 311 in either of two directions as shown by arrows 316.

The trigger mechanism 306 also includes means for triggering sequentially the electronics provided in the housing 302 and the scan head 303 at different spatial intervals. This triggering means can be of any suitable type as for example an optical scanner 321 carried within the scan head adjacent the attachment 307 and viewing an exterior planar generally vertical surface 322 extending the length of the support member 312 and having provided thereon a scale 323 in the form of a plurality of equally spaced-apart vertical marks 324 which by way of example can be black or another opaque color to stand out visually from the background of the scale 323 to provide contrast to make them readily visible to the optical reader or scanner. By providing such a scale 323 on the support member 312, the support member also serves as a ruler. Thus if desired, another support member 312 can be provided with a scale 323 which has marks which are spaced apart in a different manner. For example one ruler could have marks which are more closely spaced to take multiple images of a relatively small body of tissue as for example a small organ. Alternatively, another ruler could have a scale provided with marks which are further apart for taking sequential images of a relatively large body.

Operation and use of the ultrasound apparatus 301 may be briefly described as follows. Let it be assumed that it is desired to image an organ in the patient as for example in the abdominal region. The physician need merely grasp the housing 302 by the hand and then place the support member 312 on the skin of the patient and having the scan head 303 engage the skin of the patient at the same time. Sequential images can then be obtained and stored in the memory by moving the housing 302 with the attachment 307 carried by the scan head 303 be moved longitudinally of the support member 312 having the scale 323 thereon to cause sequential images to be taken of the organ or tissue being analyzed under the skin of the patient. Since the triggering of the images is under the control of the bars or marks carried by the scale 323, the images will be taken at different spatial intervals of the organ and will be spaced apart equally regardless of the speed of movement of the scan head 303 relative to the scale 323 carried by the support member 312. The images so taken can be stored in a random access memory card carried in the housing 302 as hereinbefore described. These images can also be stored in the memory within the electronics of the ultrasonic apparatus and then can be replayed to display a kinetic image on the display 326 carried by the housing 302. Alternatively, the non-volatile random access memory card can be removed and inserted into a notebook computer or other device to display the successive images to obtain a kinetic image of the organ being examined.

As also explained previously, depending on the size of the organ, different spatial intervals can be selected depending on the size of the organ by merely exchanging the support member 312 being utilized. Support members 312 providing the desired spacing can then be substituted one for the other to obtain the desired kinetic imaging.

It should be appreciated in connection with the present invention that various types of triggering devices can be utilized. For example a mechanical wheel traveling with the housing could be utilized for triggering the image taking. Magnetic triggering also could be readily used in such a device.

Figure 10:
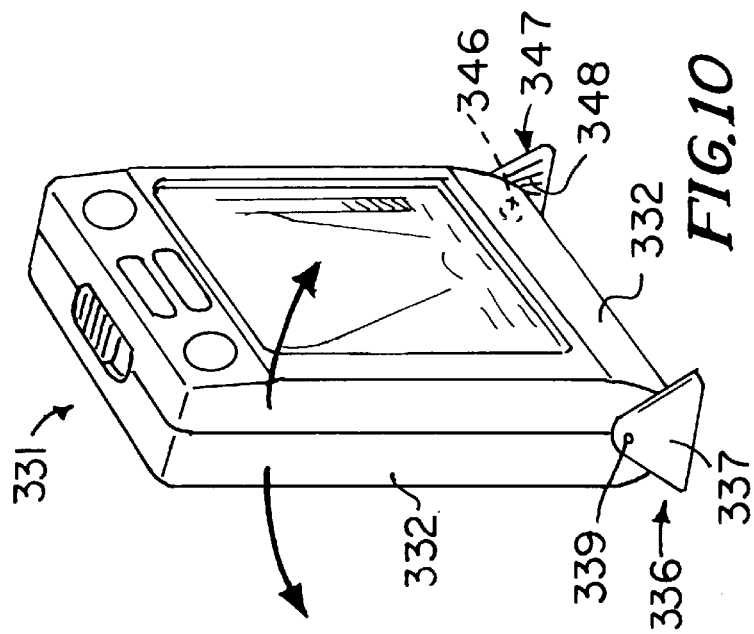
FIG. 10 is an isometric view of an ultrasonic apparatus incorporating the present invention for obtaining kinetic imaging utilizing sector scanning.

Another embodiment of the ultrasonic apparatus of the present invention making possible kinetic imaging is shown in FIG. 10. The ultrasound apparatus 331 shown therein consists of a housing 332 with a detachable scan head 333 of the type hereinbefore described. The triggering mechanism 336 of this embodiment of the ultrasonic apparatus 331 includes first and second pairs of spaced-apart triangular shaped feet 337 and 338 provided on opposite ends of the scan head 333. The feet 337 and 338 are pivotably connected to the scan head 333 by pins 339. The feet 337 and 338 have lower planar surfaces 341 which are spaced apart and are parallel to each other and are generally in alignment with the lower extremity of the scan head 333. An optical reader 346 is carried by one end of the scan head 333 and is adapted to view an arcuate scale 347 in the form of angularly spaced apart marks 348 carried by the interior surface of the foot 338 and being visible to the optical reader 346. The marks 348 are angularly spaced apart so that as the housing and the scan head 332 and 333 are pivoted with respect to the pins 339 carried by the feet 337 and 338, the optical reader will sequentially view the marks to cause triggering of the electronics and the taking of successive images spaced apart equally approximately radially in a sector-shaped scan of the tissue. Scans which are more closely spaced in distance or farther apart radially can be achieved by replacing the foot 338 with other feet having different scales thereon which can be scanned by the optical reader 346. As explained previously, these images can be stored in the memory within the electronics or alternatively can be stored in a separate non-volatile memory card inserted into the housing 332 and thereafter viewed at a separate location on a separate apparatus as for example a notebook computer. Such sector-shaped kinetic imaging may be very desirable where it is difficult to achieve linear imaging because of space constraints. For example sector-shaped kinetic imaging may very well be appropriate for imaging carotid vessels.

Kinetic imaging is used as a method of approximating 3-dimensional space with 2-dimensional images by making a plurality of images of an organ being examined along the length of the organ at equal distance intervals. The resulting images are played back sequentially and provide a sense of 3-dimensional imaging of the organ in the selected location. Cannulas and probes can be accurately guided into the appropriate depth of penetration by aligning the target with the ultrasound displayed image. The apparatus and method of the present invention is particularly useful for emergency medicine. It also can be very useful in obstetrics and gynecology, soft tissue biopsies, vascular access and cardiology.

Figure 11:
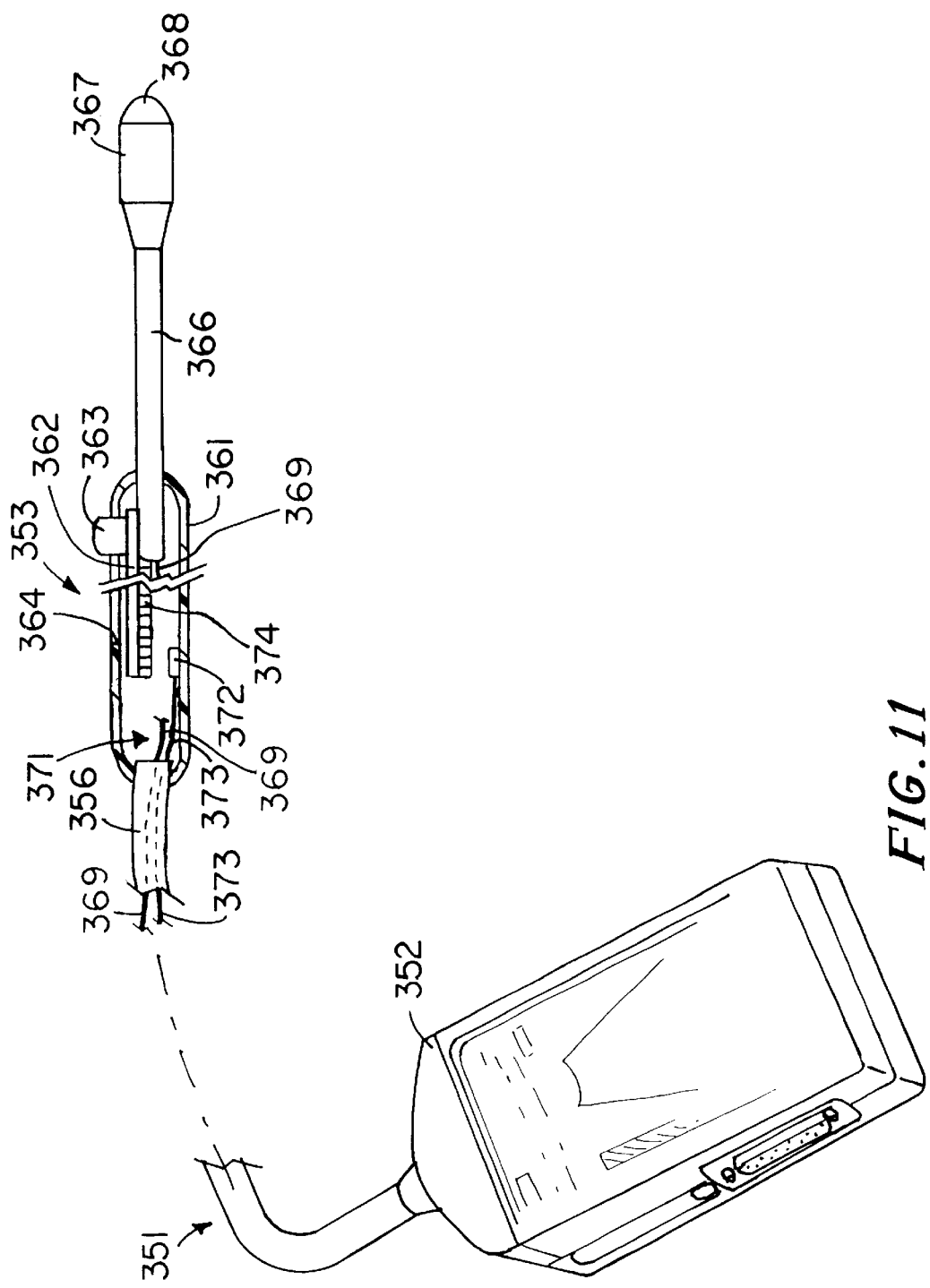
FIG. 11 is an isometric view of another embodiment of an ultrasonic apparatus incorporating the present invention incorporating a probe.

Still another ultrasound apparatus incorporating the present invention is the ultrasound apparatus 351 is shown in FIG. 11. This ultrasound apparatus 351 also includes a hand-held housing 352 of the type hereinbefore described which encloses the electronics also hereinbefore described. The ultrasonic transducer rather than being carried by a detachable scan head attaching to the housing is carried in a probe 353 connected by a cable 356 to the housing. The probe 353 consists of a handle 361 which is of a length and size adapted to fit in the palm of the hand. The handle 361 is provided with a slider 362 slidably mounted therein longitudinally of the handle and is provided with an upwardly extending knob 363 which extends through an elongate slot 364 provided on the top side of the handle 361 and accessible by the thumb of the hand grasping the handle 361 for moving the knob 363 within the slot 364. A rigid shaft 366 is secured to the slider 362 and is slidably movable with the slider 362 and carries a probe head 367 which is provided with a conical tip 368. A transducer (not shown) is provided within the probe head 367 and can be of a conventional type. It can either be a linear transducer or a sector scan transducer.

A flexible cable 369 extends from the transducer and is connected into the cable 356. A trigger mechanism 371 of the type hereinbefore described is incorporated in the handle 361 and as shown can take the form of an optical reader 372 connected by conductors 373 to the electronics in the housing 352. The optical reader is provided for scanning a scale 374 underlying the slider 362 and which is provided with a plurality of longitudinally spaced-apart marks underlying the slider 362. Thus, as the slider is moved by operation of the knob 363 to cause longitudinal movement of the probe head 367, images are taken at spaced-apart distances. As in the previous embodiments, these images will be spaced apart in the tissue being examined at desired distance intervals independent of the speed of movement of the slider 362 under the control of the knob 363. As in the previous embodiments, these images can be played back to provide a kinetic image or alternatively can be viewed at a separate location by removal of the non-volatile memory card and using it for example in a portable computer. The ultrasound apparatus 351 provided in FIG. 11 can be utilized in a number of medical applications as for example in transrectal or transvaginal imaging as well as a variety of other applications in urology such as examining the prostate or examining parts of the alimentary canal.

It is apparent from the foregoing that there has been provided an ultrasound apparatus which has been miniaturized so it is very compact and is relatively simple to operate. The method of forming a frame by collecting all of the data utilized for making the image of a frame from transducer excitations less than thirty-three in number, preferably only one, greatly reduces power consumption. The electronics described makes it possible to increase the visual resolution obtainable to the inherent resolution of the transducer array. The electronics described also makes it possible to export the preprocessed data to be processed in an optimized fashion for display in a higher or lower resolution display unit.

What is claimed:

1. Ultrasound apparatus for examining an area of tissue in a region of interest in a body comprising a housing having a viewing aperture, an ultrasonic transducer comprised of an array of ultrasonic elements disposed in the viewing aperture and having an inherent resolution, means substantially transparent to ultrasound carried by the housing forming an impedance matching lens overlying the array and having a surface capable of being placed in contact with the body, means for supplying transmitted electrical pulses to said transducer for a single transducer excitation to introduce ultrasonic signals into the body for reflection from an area of the tissue in the region of interest, said transducer being capable of converting ultrasonic signals reflected from within the body to provide electrical signals of raw date for the area of tissue, means for digitizing and storing the electrical signals and means for processing the digitized electrical signals to form one image frame from the raw data for a single area.

2. Apparatus as in claim 1 further including means for increasing the visual resolution of the visual image to the inherent resolution of the transducer.

3. Apparatus as in claim 1 for use with a remote display unit and further including means for exporting the preprocessed raw data to the remote display unit.

4. Apparatus as in claim 1 further including means for averaging the digitized electrical signals for a plurality of raw data areas to improve the resolution of the visual image.

5. Apparatus as in claim 1 wherein said array is a linear array.

6. Apparatus as in claim 1 wherein said array is a phased array.

7. Apparatus as in claim 1 wherein said array is a curved array.

8. Apparatus as in claim 1 wherein said display is disposed in a separate display module separate from the housing.

9. Apparatus as in claim 1 wherein said display module is a cathode ray tube.

10. Apparatus as in claim 1 wherein said display is a liquid crystal display.

11. Apparatus as in claim 1 wherein said housing is formed in first and second parts, said second part being detachable from the first part, said second part having the viewing aperture therein, said array of ultrasonic elements being disposed in the viewing aperture and an impedance matching lens overlying the array of ultrasonic transducers.

12. Apparatus as In claim 11 wherein a plurality of second parts are provided with each of the second parts being usable one at a time and having a different frequency range suited for a specific imaging objective.

13. Apparatus as in claim 12 further including cooperative means including a non-volatile memory carried by the second part for informing the first part of the frequency range of the second part so that viewing can take place of the area of interest.

14. Apparatus as in claim 11 wherein said housing also includes a main module and wherein said main module and display module are formed into a mating clam-shell-like construction.

15. Apparatus as in claim 1 wherein said display is integrated into said housing.

16. Apparatus as in claim 1 further comprising a separate display module and wherein said display means is disposed in the display module and electrical circuit means interconnecting the housing with the display module.

17. Apparatus as in claim 1 wherein electrical circuit means includes an interconnecting cable.

18. Apparatus as in claim 1 for use with a probe and further including a support platform adapted to be placed on the surface of the body and being formed to receive the housing for positioning the housing for movement with respect to the support structure and the body and a carriage formed to receive the probe and slidably mounted on the support platform.

19. Apparatus as in claim 18 further including a scale on the support platform for ascertaining movement of the carriage on the support platform and a scale carried by the display corresponding to the scale on the support platform whereby the relative positioning between the probe and the region of interest in the body can be ascertained by viewing the display means.

20. Apparatus as in claim 1 wherein said housing includes means for receiving a removable memory card.

21. Apparatus as in claim 1 wherein said memory card is an industry standard modem card.

22. Apparatus as in claim 1 further including means for recording multiple images of the area of interest at spaced apart locations.

23. Apparatus as in claim 22 wherein said locations are sequential and are equally spaced apart.

24. Apparatus as in claim 23 further including means for displaying said multiple images on the display means to create a kinetic image of the region of interest.

25. Apparatus as in claim 22 wherein said means for recording multiple images at spaced apart locations includes support means for supporting the housing and being adapted to be seated on the surface of the body, said support means including means permitting the movement of the housing relative to the support means whereby different views can be taken of the region of interest.

26. Apparatus as in claim 25 wherein said means permitting movement of the housing relative to the support means permits pivotal movement.

27. Apparatus as in claim 25 wherein said means for supporting the housing and permitting movement of the housing relative to the support means is constructed to permit linear movement.

28. Apparatus as in claim 25 further including means actuated by movement of the housing relative to the support means to cause the taking of sequential images as the movement is occurring.

29. Apparatus as in claim 28 wherein said means includes a trigger mechanism.

30. Apparatus as in claim 29 wherein said trigger mechanism is an optical reader.

31. Apparatus in claim 1 wherein the means for collecting the digitized electrical signals includes means for selecting a wave packet of electrical signals in space having a center, means for selecting a point (x,y) in the wave packet, means for calculating the distance from the center of the wave packet around the point (x,y) to a selected element of the array of the transducer, means for converting distance to time to select the sample points, means for interpolating the phase and magnitude between the nearest sample points and the point to be calculated to determine the corrected phase and magnitude of the point being calculated, means for repeating the same sequence of steps for each of the ultrasonic elements of the array of the transducer and means for summing the calculated points of corrected phase and magnitude.

32. A method as in claim 31 wherein the step of collecting the digitized electrical signals includes the steps of selecting a wave packet of electrical signals in space having a center, selecting a point (x,y) in the wave packet, calculating the distance from the center of the wave packet around the point (x,y) to a selected element of the array of the transducer, interpolating the phase and magnitude between the nearest adjacent points in the wave packet to determine the corrected phase and magnitude of the point being calculated, repeating the same steps for each of the ultrasonic elements of the array of the transducer and summing the calculated points of corrected phase and magnitude to provide an image.

33. A method as in claim 32 further including incrementing x (x,y) to obtain the center of the next wave packet to be utilized for calculating additional points of the image.

34. Ultrasound apparatus for examining tissue in a region of interest in a body comprising a housing having a viewing aperture, an ultrasonic transducer comprised of an array of ultrasonic elements disposed in the viewing aperture and having an inherent resolution, means substantially transparent to ultrasound carried by the housing forming an impedance matching lens overlying the array and having a surface capable of being placed in contact with the body, means for supplying transmitted electrical pulses to said at least one transducer for single transducer excitation but less than six to introduce ultrasonic signals into the body for reflection from the tissue in the region of interest, said transducer being capable of converting ultrasonic signals reflected from within the body to provide electrical signals, means providing gain correction of the electrical signals in accordance with time, mixing means for providing in-phase and out-of-phase components of the gain corrected electrical signals, means for digitizing the in-phase and out-of-phase components of the electrical signals, means for collecting the digitized electrical signals to form one image for a single frame of the tissue in the region of interest in the body from transducer excitations less than thirty-three in number, memory means for storing the digitized electrical signals of the single frame by storing the magnitude, phase angle and time of receipt of each received digitized electrical signal to provide preprocessed data, display means to utilize the preprocessed data and means coupling the memory means to the display means to provide a visual image of the tissue in the region of interest in the body herein the means for collecting the digitized electrical signals includes means for selecting a wave packet of electrical signals in space having a center, means for selecting a point (x,y) in the wave packet, means for calculating the distance from the center of the wave packet around the point (x,y) to a selected element of the array of the transducer, means for converting distance to time to select the sample points, means for interpolating the phase and magnitude between the nearest sample points and the point to be calculated to determine the corrected phase and magnitude of the point being calculated, means for repeating the same sequence of steps for each of the ultrasonic elements of the array of the transducer, means for summing the calculated points of corrected phase and magnitude and means for incrementing (x,y) to obtain the center of the next wave packet to be utilized for calculating additional points of the image.

35. A method for examining tissue of an area in a region of interest in a body by the use of an ultrasound transducer comprised of an array of ultrasonic elements in which the transducer is excited by a single excitation by received ultrasonic signals to provide electrical signals, the method comprising the steps of receiving the electrical signals from the transducer of a single excitation, providing raw data of the area, digitizing and storing the electrical signals and processing the digitized electrical signals to form one image frame from the raw data of a single area of the tissue in the region of interest in the body.

36. A method as in claim 35 which includes the use of electronics and a microprocessor for controlling the electronics, further including the step of using the microprocessor for placing at least certain parts of the electronics in a sleep mode when those parts have performed their functions to conserve power.

37. A method as in claim 35 further including the step of averaging the digitized electrical signals for a plurality of raw data areas to improve the resolution of the image frame.

38. A method as in claim 35 further including providing gain correction of the electrical signals in accordance with time and providing in-phase and out-of-phase components of the gain corrected electrical signals.

39. Ultrasound apparatus as in claim 1 adapted for use with a human hand and wherein the housing is sized so it is pocket sized and adapted to be held by the human hand.

40. Ultrasound apparatus for examining an area of tissue in a region of interest in a body by the use of a human hand comprising a housing, said housing being pocket sized and being adapted to fit within a human hand, said housing having a viewing aperture and an ultrasonic transducer comprised of an array of ultrasonic elements disposed in the viewing aperture, means within the housing for supplying transmitted electrical signals to said ultrasonic transducer to introduce ultrasonic signals into the body from a single excitation to insonify said area and cause ultrasonic signals to be reflected from said isonified area, said transducer being capable of converting said ultrasonic signals of a single excitation reflected from within the body to provide electrical signals of raw date of the isonified area, a digitizer for digitizing the electrical signals to provide digitized electrical signals, a memory for storing the digitized electrical signals and a processor for processing the stored digitized electrical signals to form one image frame from the raw data of the isonified area, a visible display mounted on the housing and means within the housing for receiving the electrical signals received from the transducer and coupling the electrical signals to the visible display to provide a visual image of the tissue in the region of interest in the body.

41. Apparatus as in claim 40 wherein said display is a liquid crystal display.

42. Apparatus as in claim 40 wherein said housing is formed of first and second parts, said second part being detachable from the first part, said second part having the viewing aperture therein.

43. Apparatus as in claim 42 wherein a plurality of second parts are provided and wherein each of the second parts is usable one at a time and has a different frequency range suited for a specific imaging objective.

44. A method for examining an area of tissue in a region of interest in a body by the use of a probe comprising a pocket-sized hand held housing having a viewing aperture therein, an ultrasonic transducer comprised of an array of ultrasonic elements disposed in the viewing aperture and a display mounted on the housing and coupled to the ultrasonic transducer, the method comprising grasping the probe and moving it over the body to examine the area of tissue in the body, isonifying said area with ultrasonic energy from a single excitation to cause ultrasonic energy to be reflected from the isonified area to provide raw data of the isonified area, creating an image frame from the raw data of the isonified area and viewing the image frame being displayed on the display means while the housing is being held by the hand and being moved over the body.

45. A method as in claim 44 further including the step of displaying multiple images on the display means to create a kinetic image of the region of interest.

46. Ultrasonic apparatus for examining of an area of tissue in a region of interest in a body by the use of a human hand comprising a housing having display means mounted thereon and being pocket-sized and adapted to fit within a human hand and an ultrasonic transducer comprised of an array of ultrasonic elements adapted to be placed in contact with the body for viewing the region of interest, means for connecting the ultrasonic transducer to the housing, means within the housing coupled to the ultrasonic transducer for isonifying said area with ultrasonic energy to cause ultrasonic energy from a single excitation to be reflected from the isonified area to provide raw data of the isonified area, means for creating an image frame from the raw data of the isonified area and means for displaying a visual image of the image frame.

47. Apparatus as in claim 46 wherein said housing includes a viewing aperture and wherein said ultrasonic transducer is disposed in the viewing aperture.

48. Apparatus as in claim 46 wherein said housing is formed of first and second parts with the second part being detachable from the first part and being in the form of a scan head, said second part having a viewing aperture therein and wherein the ultrasonic transducer is disposed in the viewing aperture.

49. Apparatus as in claim 46 further including a probe and means for mounting said ultrasonic transducer in said probe and for connecting the ultrasonic transducer to the housing.

50. Apparatus as in claim 46 wherein said housing includes a main module and a display module formed as separate parts and means for detachably interconnecting the main module and the display module.

51. Apparatus as in claim 1 further Including means for providing gain correction of the electrical signals in accordance with time and a mixer for providing in-phase and out-of-phase components of the gain corrected electrical signals.

52. Ultrasound apparatus for examining an area of tissue in a region of interest in the body by use of a human hand comprising a housing, said housing being pocket sized and being adapted to fit within a human hand, said housing including a detachable part, said detachable part having a viewing aperture therein, an ultrasonic transducer comprised of an array of ultrasonic elements disposed in the viewing aperture and within the detachable part, said detachable part having a specific frequency range suited for a specific imaging objective, memory means carried by the detachable part and having incorporated in its memory the frequency range of the detachable part and means carried by the detachable part and the housing for informing the housing of the frequency range of the detachable part.

* * * * *

UNITED STATES PATENT AND TRADEMARK OFFICE
CERTIFICATE OF CORRECTION

PATENT NO. : 6,251,073 B1
DATED : June 26, 2001
INVENTOR(S) : Imran et al.

It is certified that error appears in the above-identified patent and that said Letters Patent is hereby corrected as shown below:

Column 16,
Line 50, delete "31" and replace with -- 35 --.

Signed and Sealed this

Tenth Day of September, 2002

Attest:

Attesting Officer

JAMES E. ROGAN
Director of the United States Patent and Trademark Office